United States Patent [19]

Warriner

[11] Patent Number: Plant 7,659

[45] Date of Patent: Oct. 1, 1991

[54] ROSE PLANT JACDASH

[75] Inventor: William A. Warriner, Tustin, Calif.

[73] Assignee: Bear Creek Gardens, Inc., Medford, Oreg.

[21] Appl. No.: 513,893

[22] Filed: Apr. 23, 1990

[51] Int. Cl.[5] ..... A01H 5/00

[52] U.S. Cl. ..... Plt./15

[58] Field of Search ..... Plt./15

[56] References Cited

U.S. PATENT DOCUMENTS

P. 3,272 12/1972 Byrum ..... Plt. 15

*Primary Examiner*—Howard J. Locker

*Attorney, Agent, or Firm*—Klarquist, Sparkman, Campbell, Leigh & Whinston

[57] ABSTRACT

A hybrid tea class rose plant having bright yellow flower color that is deeper than the male parent, but not as nonfading as the female parent. The plant has dark green foliage, much darker than the male parent, but not glossy like the female parent. The plant is resistant to powdery mildew and rust like the female parent. The plant also has long cutting stems and strong pleasing fragrance.

1 Drawing Sheet

The present invention relates to a new and distinct variety of rose plant of the hybrid tea class which was originated by me by crossing the variety Sunbright, U.S. Plant Pat. No. 4,438, with an unnamed breeding line.

The primary objective of this breeding was to produce a new rose variety of the hybrid tea class bearing longer stems than the female parent Sunbright, which has 12- to 14-inch stems, excellent dark green foliage, deep yellow flower color, but with the better color than the male parent, which has very long stems (26 inches long), very pale yellow flower color and light green foliage. The objective was substantially achieved along with other desirable improvements as evidenced by the following unique combination of characteristics which are outstanding in the new variety and which distinguish it from its parents as well as from all other varieties of which I am aware:

1. Bright yellow flower color — deeper than the male parent, but not as nonfading as the female parent.
2. Dark green foliage — much darker than the male parent, but not glossy like the female parent.
3. Resistance to powdery mildew and rust like the female parent, but not like the male parent.
4. Long cutting stems— midway between the parents.
5. Strong pleasing fragrance.

Asexual reproduction of this new variety by budding, as performed at Somis, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with The Royal Horticultural Society (London) Colour Chart except where ordinary dictionary significance of color is indicated.

Parentage:

*Seed parent.*—Sunbright, U.S. Plant Pat. No. 4,438.

*Pollen parent.*—An unnamed breeding line.

Classification:

*Botanical.*—*Rosa hybrida.*

*Commercial.*—Hybrid tea.

FLOWER

Observations made from specimens grown at Somis, Calif., from Jun. to Sep., 1989.

Blooming habit.—Recurrent.

Bud:

*Size.*—About 1½ inches long when petals start to unfurl.

*Form.*—The bud form is long, pointed ovoid.

*Color.*—When sepals first divide, the bud color is Yellow Orange Group 21A. When half blown, the upper and lower sides of the petals are Yellow Orange Group 21A to B fading at the outer petals to Yellow Orange Group 21C to D.

*Sepals.*—Color: Green Group 138B. Surface texture: Sepals are covered with fine hairs. There are three lightly appendaged sepals. There are two unappendaged sepals with hairy edges.

*Receptacle.*—Color: Green Group 138B. Shape: Funnel. Size: Small. Surface: Smooth.

*Peduncle.*—Length: Medium, averaging about 2 to 2½ inches. Surface: Smooth. Color: Light green. Strength: Stiff, erect.

Bloom:

*Size.*—Large. Average open diameter is 4½ inches.

*Borne.*—Singly.

*Stems.*—Long. Average length is 18 to 22 inches.

*Form.*—When first open, bloom is high center. Permanence of bloom flattens as it opens, and outer petals curl back.

*Petalage.*—Number of petals under normal conditions: 20–25.

*Color.*—The upper and reverse sides of the petals are Yellow Orange Group 21A to B with the color fading on the outer petals to Yellow Orange Group 21C to D. The base of the petals is Green white half moon at the point of petal attachment. The major color on the upper side is Yellow Orange Group 21A to B.

*Variegations.*—None.

*Discoloration.*—No general tonality change at the end of the first day. At the end of the third day, general fading of color intensity on the outer petals.

*Fragrance.*—Strong.

Petals:

*Texture.*—Thick.

*Shape.*—Deltoid.

*Form.*—Tips slightly recurved.

*Arrangement.*—Imbricated, with no petaloids in the center.

*Persistence.*—Petals drop off cleanly before drying.

*Lastingness.*—On the plant: Long, about 3 to 5 days. As a cut flower: Long, about 7 days.

Reproductive parts:

*Anthers.*—Size: Large. Quantity: Many. Color: Yellow. Arrangement: Regular around styles.

*Filaments: Color: Reddish brown.*

*Pollen.*—Color: Gold yellow.

*Styles.*—Color: Light yellow.

*Stigmans: Color: Red.*

Plant form: Bush.

Plant growth: Vigorous, upright,

Foliage:

*Number of leaflets on normal mid-stem leaves.*—5.

*Size.*—Large, from tip of 5th leaflet to base of stipule is about 7 to 8 inches on largest leaves.

*Quantity.*—Normal.

*Color.*—New foliage: Bronze red. Old foliage: Dark green, close to Green Group 139A.

Leaflets:

*Shape.*—Oval pointed.

*Texture.*—Upper side: Leathery.

*Edge.*—Serrated.

*Serration.*—Single, small.

*Petiole rachis.*—Color: Green.

*Petiole underside.*—Smooth with an occasional prickle.

*Stipules.*—Less than about ½ inch, bearded.

*Disease resistance.*—Resistant to rust and powdery mildew, susceptible to blackspot at Somis, Calif.

Wood:

*New wood.*—Color: Reddish. Bark: Rough.

*Old wood.*—Color: Green. Bark: Smooth.

Prickles:

*Quantity.*—Ordinary quantity on main canes from base and on laterals from main canes.

*Form.*—Medium, straight to hooked slightly downward.

*Color when young.*—Red.

*Color when mature.*—Light brown.

Small prickles:

*Quantity.*—None on main stalks and on laterals.

I claim:

1. A new and distinct variety of rose plant of the hybrid tea class, substantially as herein shown and described, characterized particularly as to novelty by the unique combination of its long stems which make it an ideal cut rose for gardeners, deep green disease resistant foliage, bright yellow flower color, strong upright habit of growth, strong pleasing fragrance, and good petal substance.

* * * * *

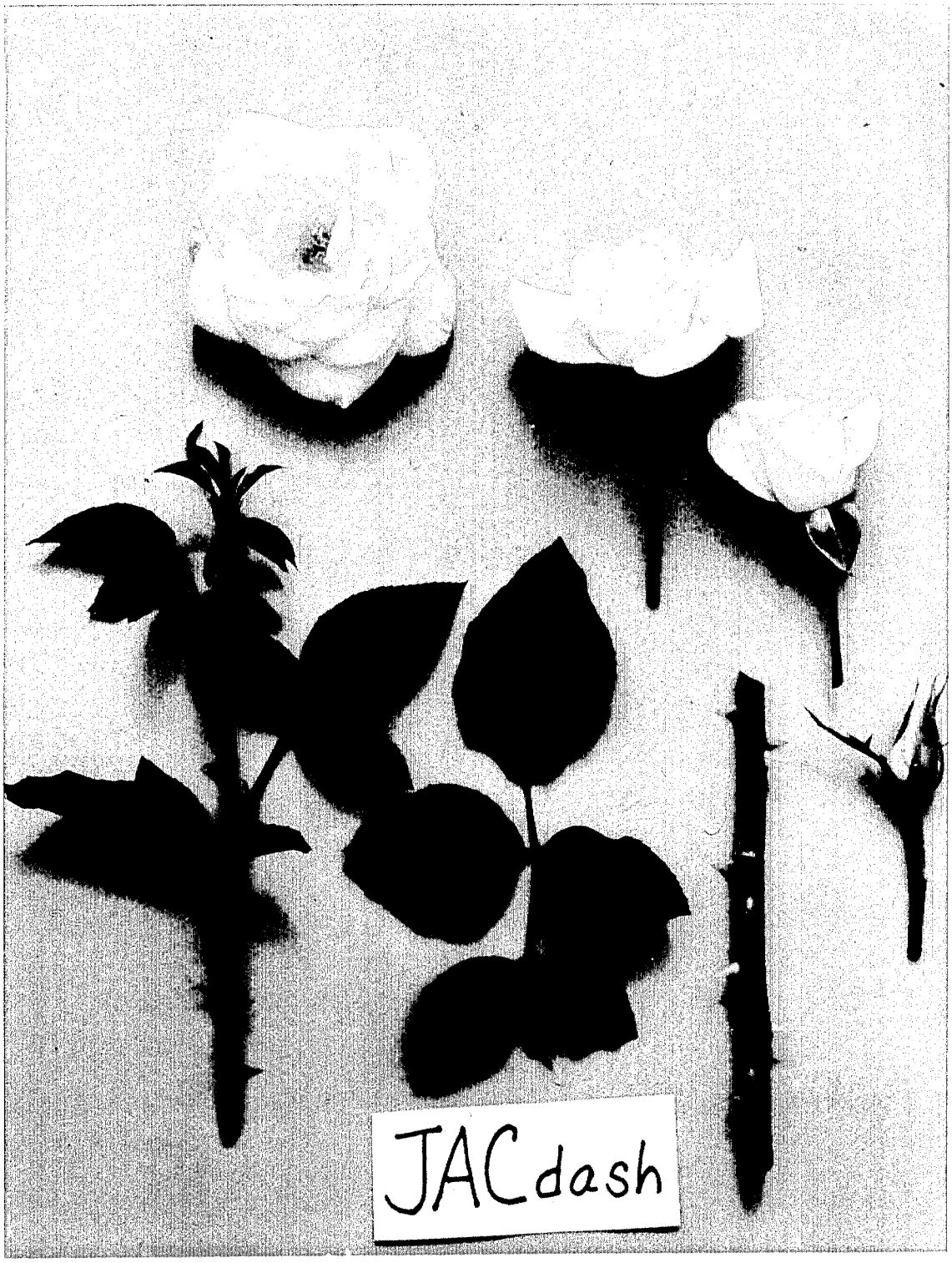
JACdash